US006525333B1

(12) United States Patent
Hooker et al.

(10) Patent No.: US 6,525,333 B1
(45) Date of Patent: Feb. 25, 2003

(54) SYSTEM AND METHOD FOR INSPECTING CONTAINERS WITH OPENINGS WITH PIPELINE IMAGE PROCESSING

(75) Inventors: Jeff Hooker, Melbourne, FL (US); Timothy Hebert, Orlando, FL (US)

(73) Assignee: Intelligent Machine Concepts, L.L.C., Titusville, FL (US)

( * ) Notice: Subject to any disclaimer, the term of this patent is extended or adjusted under 35 U.S.C. 154(b) by 0 days.

(21) Appl. No.: 09/618,344

(22) Filed: Jul. 18, 2000

(51) Int. Cl.$^7$ .............................................. G01N 21/88
(52) U.S. Cl. ........................... 250/559.45; 250/559.46; 250/223 B; 382/142; 382/143
(58) Field of Search ....................... 250/559.45, 559.46, 250/223 R, 223 B; 209/524, 526; 382/141, 142, 169, 170, 209, 143, 155, 159, 226, 227, 302, 303; 356/239.4, 239.7, 239.8, 240.1; 348/127

(56) References Cited

U.S. PATENT DOCUMENTS

| | | | |
|---|---|---|---|
| 3,848,742 A | * 11/1974 | Krenmayr | 209/526 |
| 3,923,158 A | 12/1975 | Fornaa | 209/75 |
| 4,697,245 A | 9/1987 | Kara et al. | 364/552 |
| 4,786,801 A | 11/1988 | Shay | 250/223 |
| 4,811,251 A | 3/1989 | Minato | 364/552 |
| 4,882,498 A | 11/1989 | Cochran et al. | 250/571 |
| 4,906,099 A | 3/1990 | Casasent | 356/394 |
| 4,924,107 A | * 5/1990 | Tucker | 250/559.46 |
| 5,033,096 A | * 7/1991 | Morrison et al. | 382/152 |
| 5,051,825 A | * 9/1991 | Cochran et al. | 358/151 |
| 5,280,436 A | 1/1994 | Kubota et al. | 364/559 |
| 5,369,713 A | * 11/1994 | Schwartz et al. | 382/142 |
| 5,371,690 A | 12/1994 | Engel et al. | 364/570 |
| 5,412,203 A | 5/1995 | Toyama | 250/223 |
| 5,440,385 A | 8/1995 | Fein et al. | 356/240 |
| 5,451,773 A | * 9/1995 | Triner et al. | 250/233 B |
| 5,591,462 A | 1/1997 | Darling et al. | 425/173 |
| 5,699,152 A | 12/1997 | Fedor et al. | 356/237 |
| 5,742,037 A | 4/1998 | Scola et al. | 235/454 |
| 5,764,874 A | 6/1998 | White | 396/155 |
| 5,807,449 A | 9/1998 | Hooker et al. | 156/64 |
| 5,818,443 A | 10/1998 | Schott | 382/141 |
| 5,880,772 A | 3/1999 | Kalnajs et al. | 348/87 |
| 5,901,241 A | 5/1999 | Koljonen et al. | 382/150 |
| 5,912,776 A | 6/1999 | Yaginuma | 359/850 |
| 5,936,353 A | 8/1999 | Triner et al. | 315/112 |
| 6,018,562 A | * 1/2000 | Willson | 378/9 |
| 6,134,343 A | * 10/2000 | Nichani | 382/141 |

FOREIGN PATENT DOCUMENTS

WO    WO 96/41299    12/1996    ............ G06K/9/00

OTHER PUBLICATIONS

Patent Abstracts of Japan, vol. 2000, No. 05, Sep. 14, 2000 and JP 2000 055827A (Hitachi Eng. CO. Ltd.), Feb. 25, 2000.

"100 Percent Visually Inspected Packages," Robotics World, Atlanta, Georgia, US, vol. 3, No. 8, Jul. 1, 1985, p. 36.

* cited by examiner

Primary Examiner—Robert H. Kim
Assistant Examiner—Glen Kao
(74) Attorney, Agent, or Firm—Allen, Dyer, Doppelt, Milbrath & Gilchrist, P.A.

(57) ABSTRACT

A system and method of the present invention allows the inspection of an object having an annular opening, such as a container or can, and uses a plurality of cameras that acquire grayscale images of arcuate sectors that together comprise a circumferential area within the opening. A processor is connected to the plurality of cameras for receiving the grayscale images and determining defects within the container based on contrast differences and grayscale intensity. The invention allows smart analysis of defects using qualitative inspections and quantitative measurements at higher speeds.

39 Claims, 16 Drawing Sheets

FIG. 7.
SIDE CAMERA 1
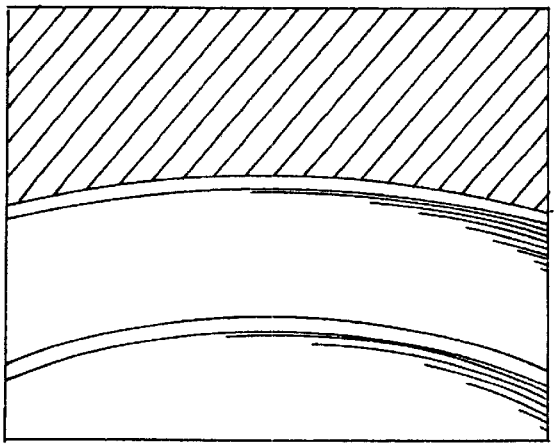
SIDE CAMERA 2
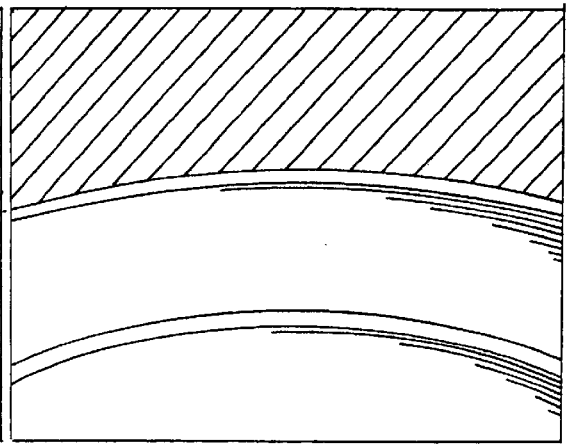
SIDE CAMERA 3
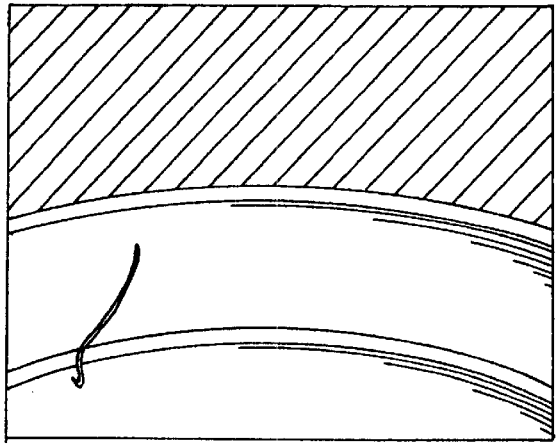
SIDE CAMERA 4
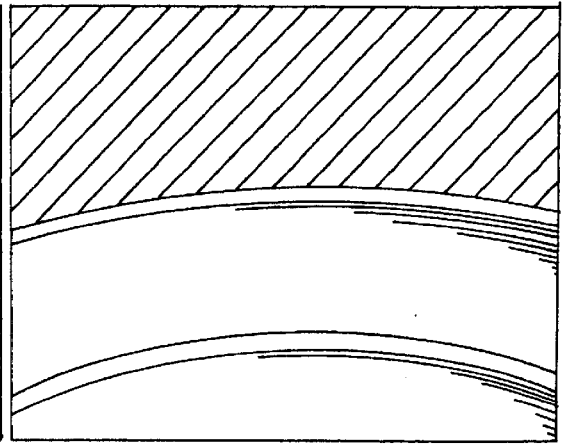
TOP CAMERA
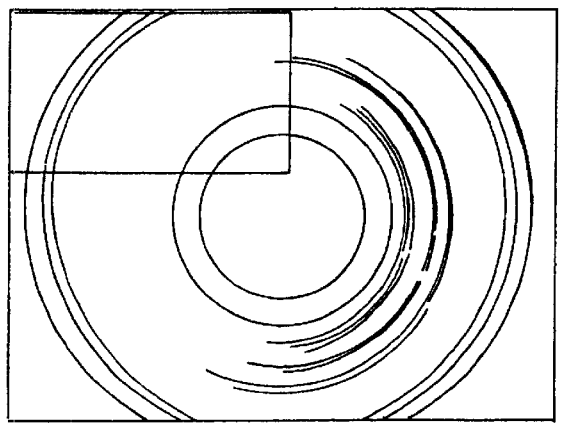

VISUAL IMAGE
PROCESSED IMAGE
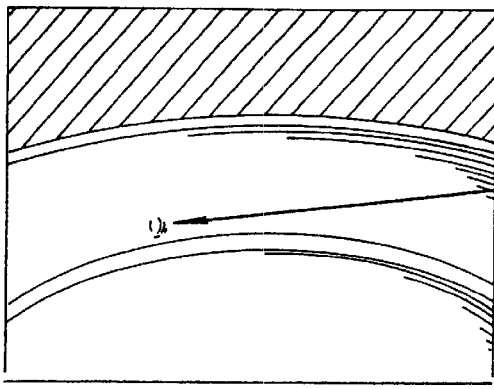
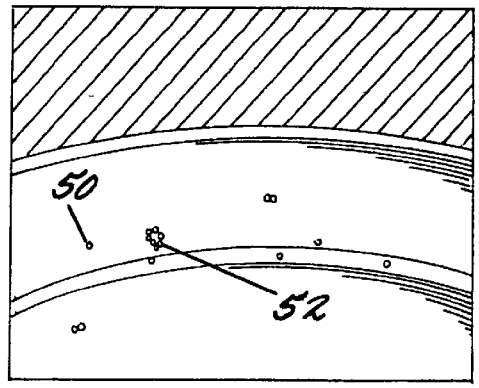
*FIG. 8A.*
*FIG. 8B.*
NECK PUCKER
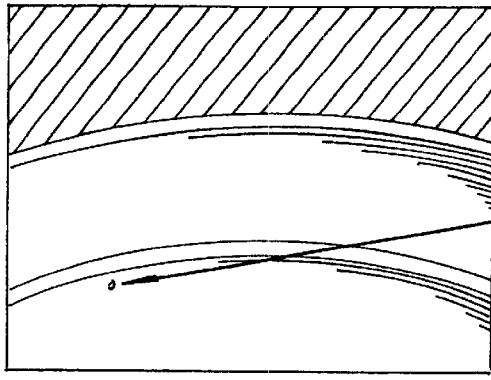
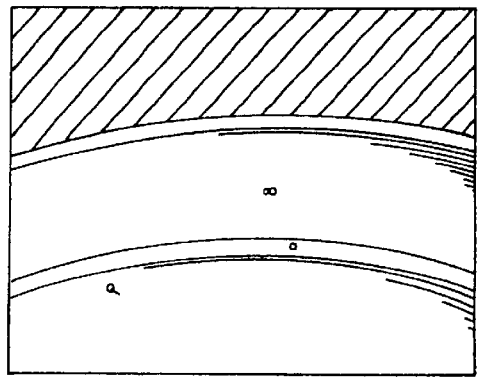
*FIG. 9A.*
*FIG. 9B.*
HOLE-IN-SIDEWALL
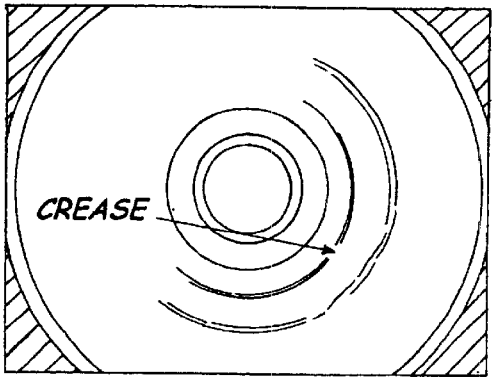
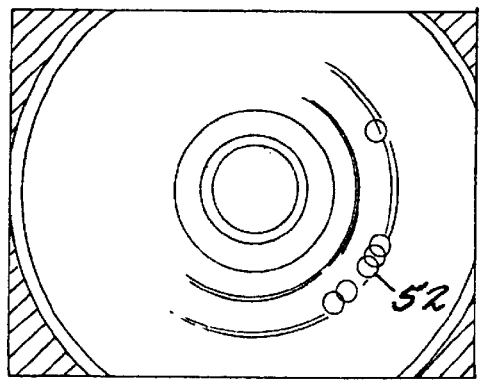
*FIG. 10A.*
*FIG. 10B.*
SIDEWALL CREASE VISUAL IMAGE PROCESSED IMAGE
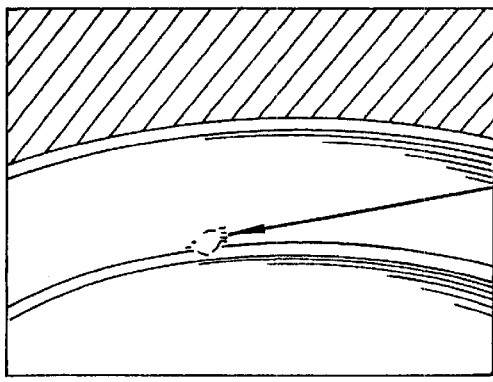
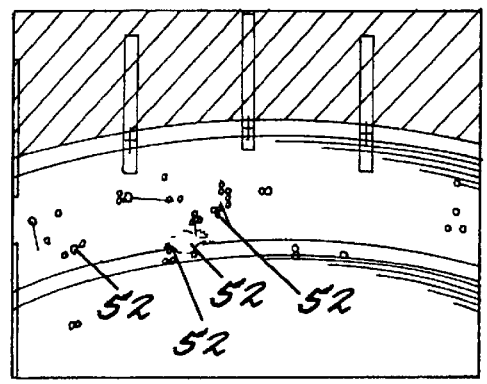
FIG.11A.  FIG.11B.
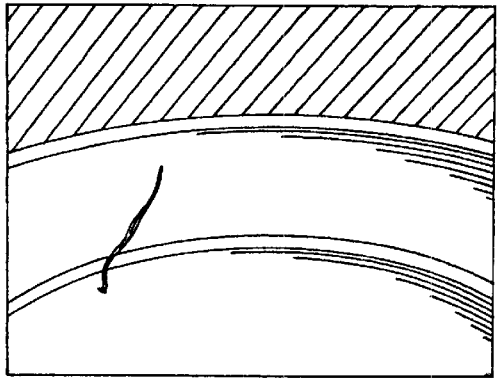
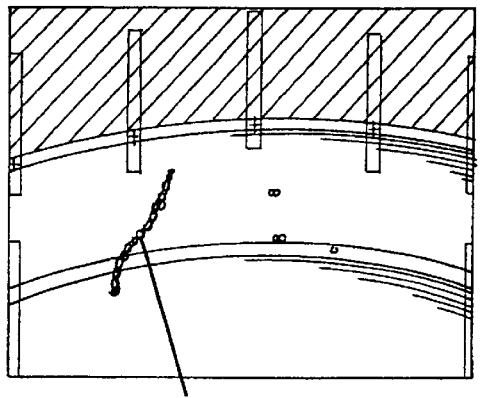
FIG.12A.  FIG.12B.

VISUAL IMAGE

PROCESSED IMAGE

SYSTEM AND METHOD FOR INSPECTING CONTAINERS WITH OPENINGS WITH PIPELINE IMAGE PROCESSING

FIELD OF THE INVENTION

This invention relates to the field of inspection, and more particularly, this invention relates to the field of inspecting containers such as cans with open tops.

BACKGROUND OF THE INVENTION

Container inspection is becoming increasingly important as customers demand increased quality and lower cost products. The use of computers in the inspection process has increased these requirements. Some systems use computerized imaging systems. For example, one system uses a conversion of image data into binary values to search for defects. For example, U.S. Pat. No. 4,924,107 to Tucker discloses a system for inspecting cans where a plurality of horizontal regions on the inside surface of an object, such as an aluminum beverage can, are inspected. This system converts images to binary values and processes the values. Other systems have similar binary value algorithms.

Greater control, however, over the can inspection process in the internal areas of the can, such as near the top, are desired using similar metrology and grayscale analysis without complicated binary conversion algorithms.

SUMMARY OF THE INVENTION

The present invention is advantageous and provides non-contact, on-conveyor, real-time, 100% gauging and defect detection system for a container, such as beverage containers and cans. The system of the present invention identifies random production of anomalies that make cans rejectable and detects internal mechanical defects, surface defects, and contamination with foreign objects on the full 360° interior of the can at line speeds to 3,000 CPM. Neck pucker, hole-in-sidewall, thumb dents, sidewall creases, ink stains and missing internal coatings can be determined and cans rejected if necessary.

In accordance with the present invention, the system inspects an object, such as a container or can, having an annular opening, and uses a plurality of cameras that acquire grayscale images of arcuate sectors that together comprise a circumferential area within the opening. A processor is connected to a plurality of cameras for receiving the grayscale images and determining defects within the container based on contrast differences in the grayscale intensity. Another camera can be positioned substantially above the opening for acquiring a top grayscale image of the opening. The processor determines defects in the top grayscale image and the grayscale images of arcuate sectors simultaneously.

In still another aspect of the present invention, a memory is associated with the processor for storing within a knowledge base of a computer memory the various rules for determining when a defect exists based on the contrast differences and grayscale intensity. The cameras can comprise charge coupled device (CCD) cameras. A strobe light is positioned at the inspection station for illuminating the container opening as containers are fed by a conveyor that advances a plurality of cylindrical containers along a redetermined path of travel into the inspection station.

An eject mechanism ejects a container from he conveyor after determining that any defects are serious enough to make the container defective. This object mechanism could comprise an air blow off mechanism.

In still another aspect of the present invention, the conveyor includes a vacuum assist mechanism to aid in retaining containers onto the conveyor by vacuum. A method is also disclosed for acquiring a plurality of grayscale images of arcuate surface sectors that together comprise a circumferential area inside the opening of the object and then processing the grayscale images to determine defects in the objects. The object can comprise the container, can or other object.

BRIEF DESCRIPTION OF THE DRAWINGS

Other objects, features and advantages of the present invention will become apparent from the detailed description of the invention which follows, when considered in light of the accompanying drawings in which:

FIG. 7 is a type of user screen having images that could be displayed and showing the four side images and a top image.

FIGS. 8A and 8B through 14A and 14B are visual images and process images showing examples of various defects.

DETAILED DESCRIPTION OF THE PREFERRED EMBODIMENTS

The present invention is advantageous and provides an inspection system for containers, such as the normal 12-ounce aluminum beverage cans that are formed as two pieces, with the formed body and a top later added. The system provides an inspection module that effectively and reliably identifies random production anomalies and rejects those cans that are considered to be defective. The system effectively detects internal mechanical damage and defects, surface-finish defects and contamination and foreign objects on the full, 360° interior of the can at line speeds up to 3,000 CPM.

Using a processor, such as a PC and memory for a historical database and knowledge base, current and historical data and other defect data can be displayed on a graphical user interface (GUI), or sent to a networked SPC system for off-line analysis. As described below and shown in the figures, the system can reliably differentiate between visual anomalies and defects that concern neck pucker, hole-in-sidewall, thumb dents, sidewall creases, ink stains and missing internal coatings, such as a lack of enamel coating.

Figure 5:
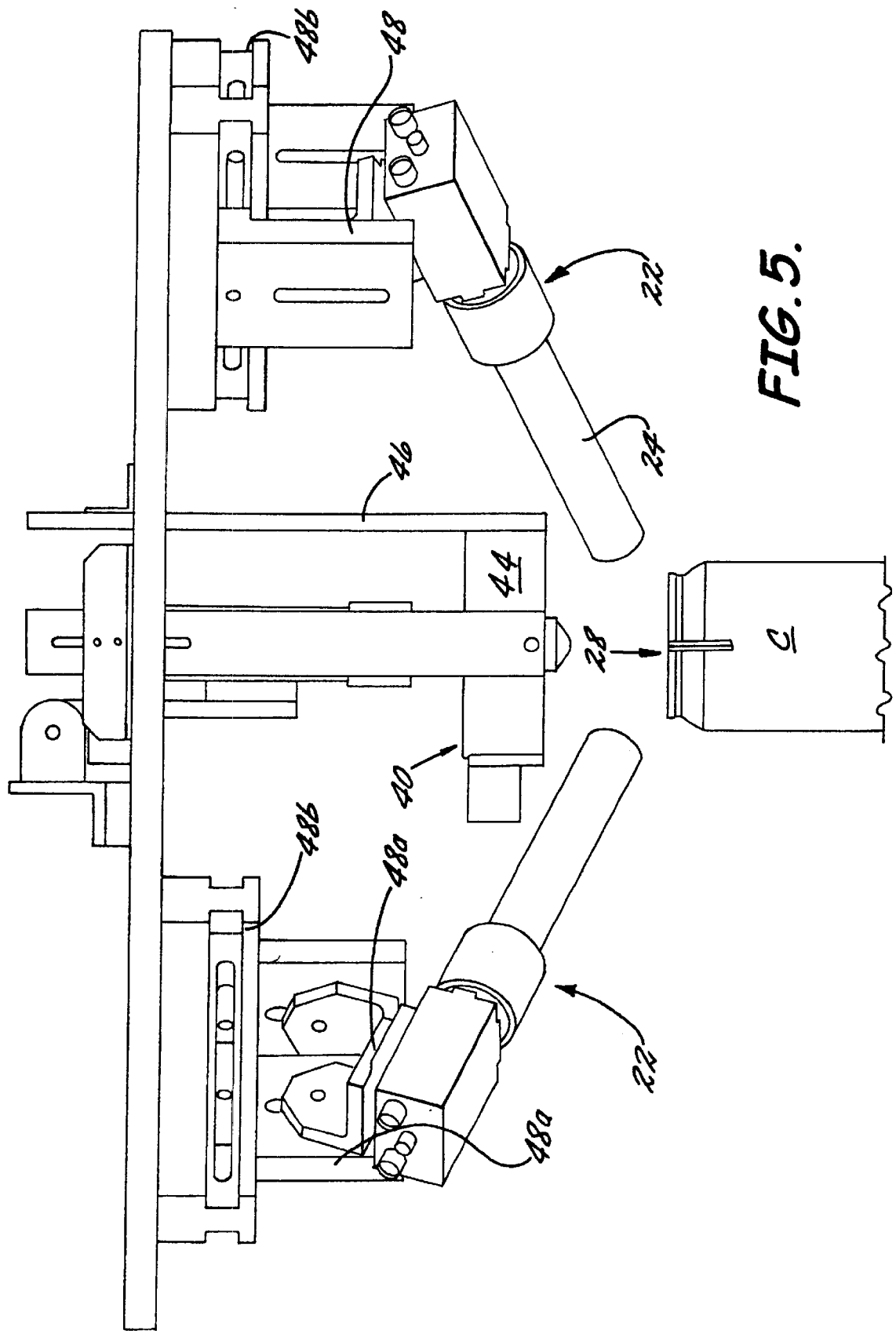
FIG. 5 is an elevation view of the cameras and lenses shown in FIG. 3.
Figure 6:
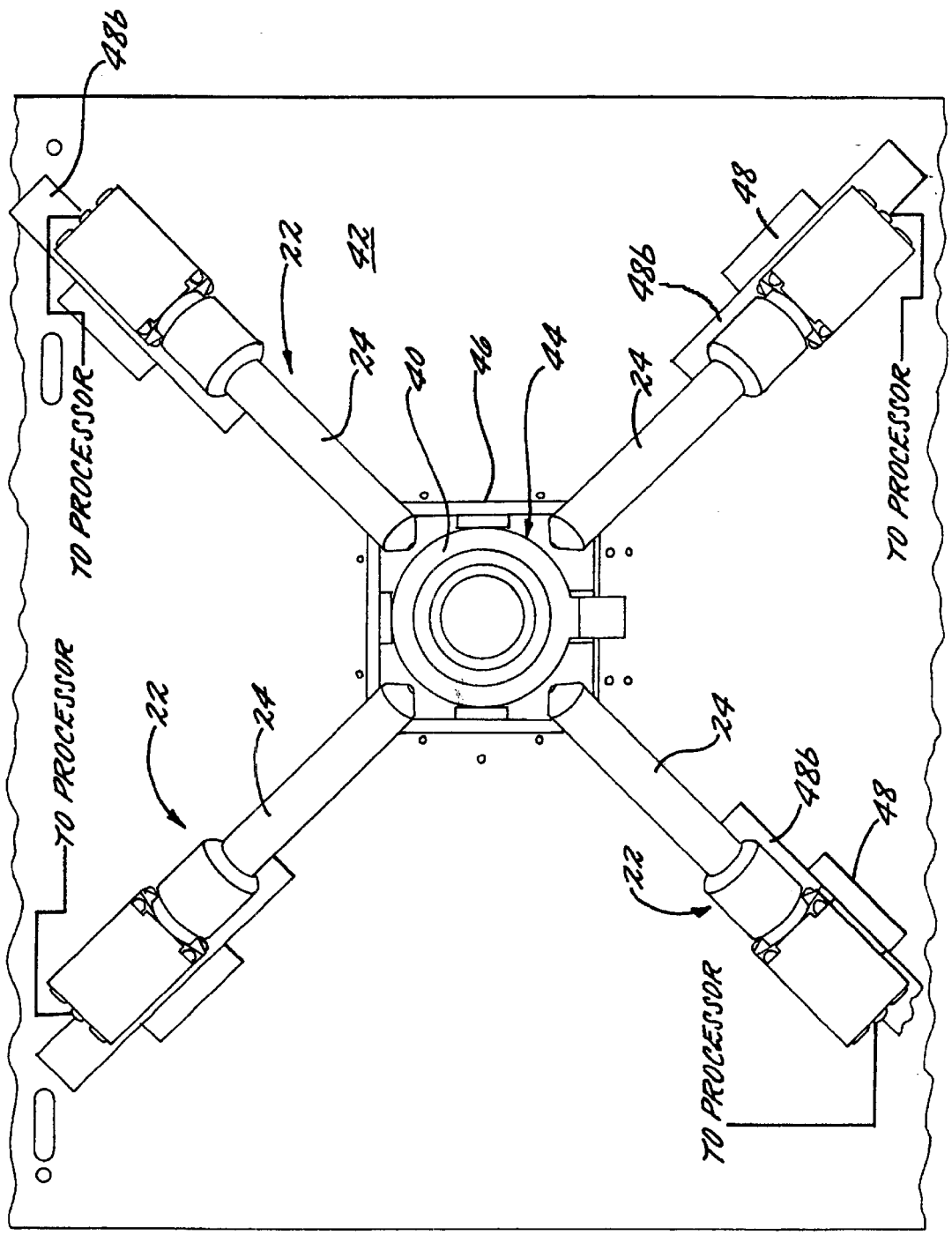
FIG. 6 is a top plan view of the inside of the inspection station showing the side cameras.
Figure 13A:
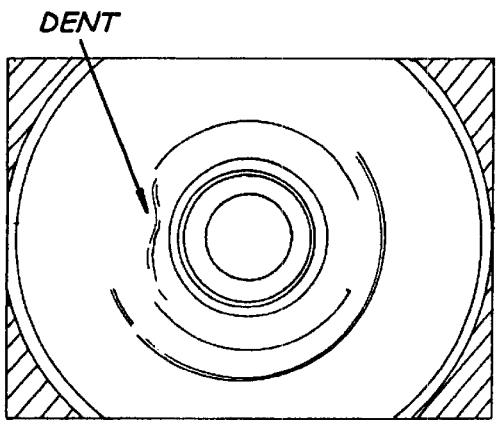
Figure 13B:
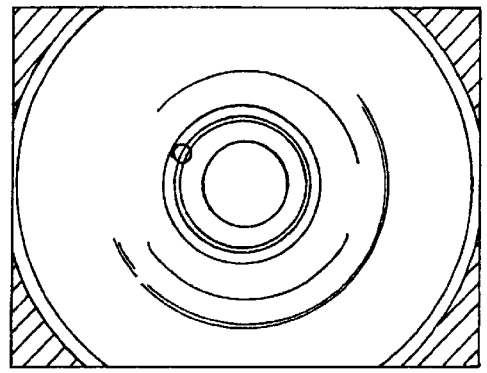

The system of the present invention uses four side cameras 22, each having an attached wide angle lens 24 (FIG. 6), and a top camera 26 positioned for obtaining a top image 28 (FIG. 5). Each side camera 22 acquires grayscale images of arcuate sectors and each comprise a circumferential area within the opening. Thus, the cameras (FIG. 6) acquire quadrant sectors, each a little over 90° with about 20% overlap with the adjacent grayscale image acquired from adjacent cameras. If only three cameras are used, there would be less overlap and the angular image spread more. Thus, four cameras have been found acceptable to obtain the necessary grayscale images. However, more than five cameras can also be used.

The top grayscale image is acquired from a top camera (FIGS. 5 and 6) and the wide angle lens. A processor is connected to the cameras for receiving the grayscale images, and determining defects within the container based on contrast differences and grayscale intensity.

Figure 1:
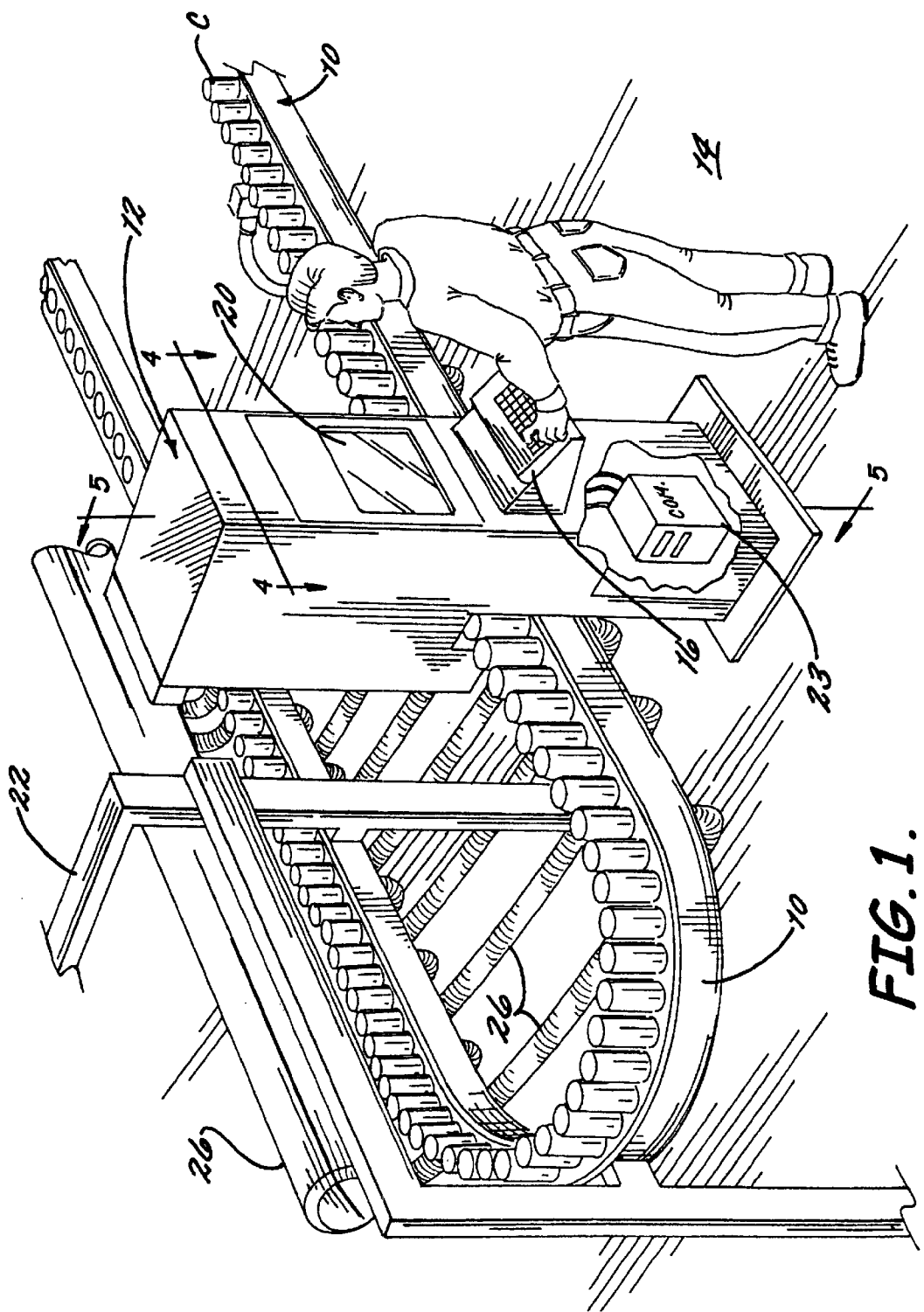
FIG. 1 is an isometric view of the system of the present invention showing an overall conveyor and inspection station, where an operator monitors and controls the inspection process.

Referring now to FIG. 1, the overall large components used in the system and method of the present invention are illustrated. A conveyor 10 holds the cans in vertical orientation and adjacent to each other, and advances the plurality of cans C along a predetermined path of travel defined by the conveyor 10 into an inspection station generally indicated at 12. Although the term "cans" is used throughout the description, other containers could be cylindrical, and other configurations with openings can be inspected by the system. The inspection station 12 can be a separate unit that mounts over the conveyor 10 and is bolted to a floor 14. An operator console, such as a keypad 16 and/or touch screen 20, can be mounted on the inspection station, although it is not necessary. The conveyor could be mounted on an appropriate frame 22 and suspension as known to those skilled in the art. The processor 23, such as a personal computer, could be mounted exterior to the unit or within the unit, as illustrated.

Figure 2:
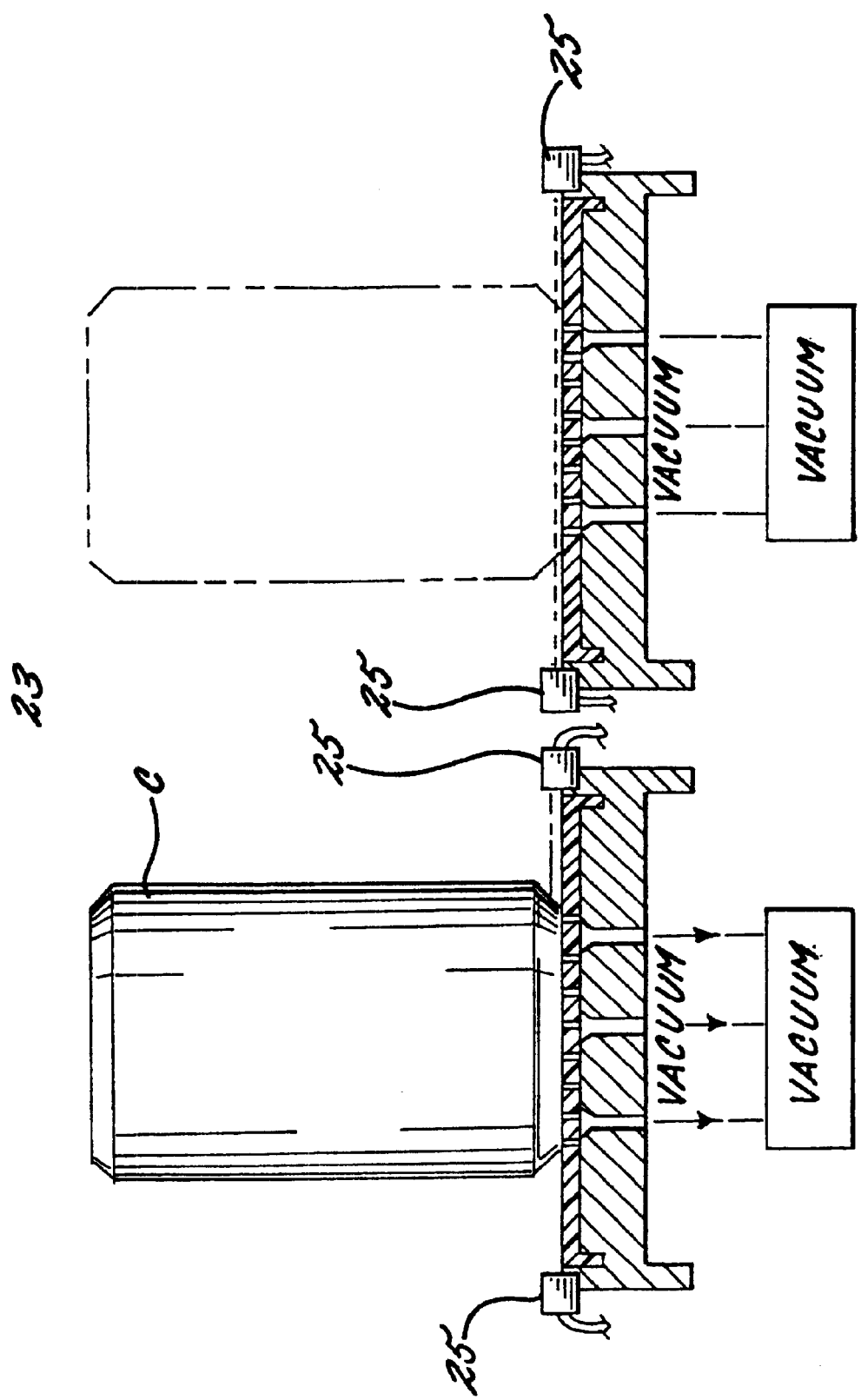
FIGS. 2A and 2B show the conveyor with a vacuum draw for aiding in holding containers onto the conveyor, and a sensor mechanism.

In one aspect of the present invention, the conveyor 10 includes a number of segments having vacuum holes (FIGS. 2A and 2B) that connect to a vacuum system to allow vacuum to be drawn from the top surface of the conveyor to retain a can C against the top surface. The cans also typically include a bottom bevel, although it is not necessary for the present invention, such that hen two cans are positioned in close proximity and touch each other, an open triangular area is formed and can be used with a sensor 25 to indicate the presence of cans (FIGS. 2A and 2B).

The conveyor 10 could be belt-driven to move the cans. Additionally, the vacuum could apply only minimal drawing force for can stability only, and cans could be advanced by pressure exerted from adjacent cans on a more stationary conveyor. It is also possible to use a conveyor that forces air upward against the cans, such that each can "floats" on a conveyor. Thus, if a straight line stationary conveyor is used, or a curved stationary conveyor with side rails, the cans "float" on the conveyor and are pushed along the air cushioned conveyor and into the inspection station 12. Other conveyors could be used as suggested by those skilled in the art for moving cans into the inspection station.

A number of different sensors 25 could be used, such as a through beam sensor (not shown) (FIGS. 2A and 2B), such that when the "open" or triangular area defined by adjacent bottom bevels of the two cans passes through the beam sensor, the light passes from the light source through an area defined by the triangular area and is received by a light receptor. This type of sensor could be connected to the processor 23 to perform the functions of the system and method of the present invention and indicate automatically the presence of a can.

Figure 3:
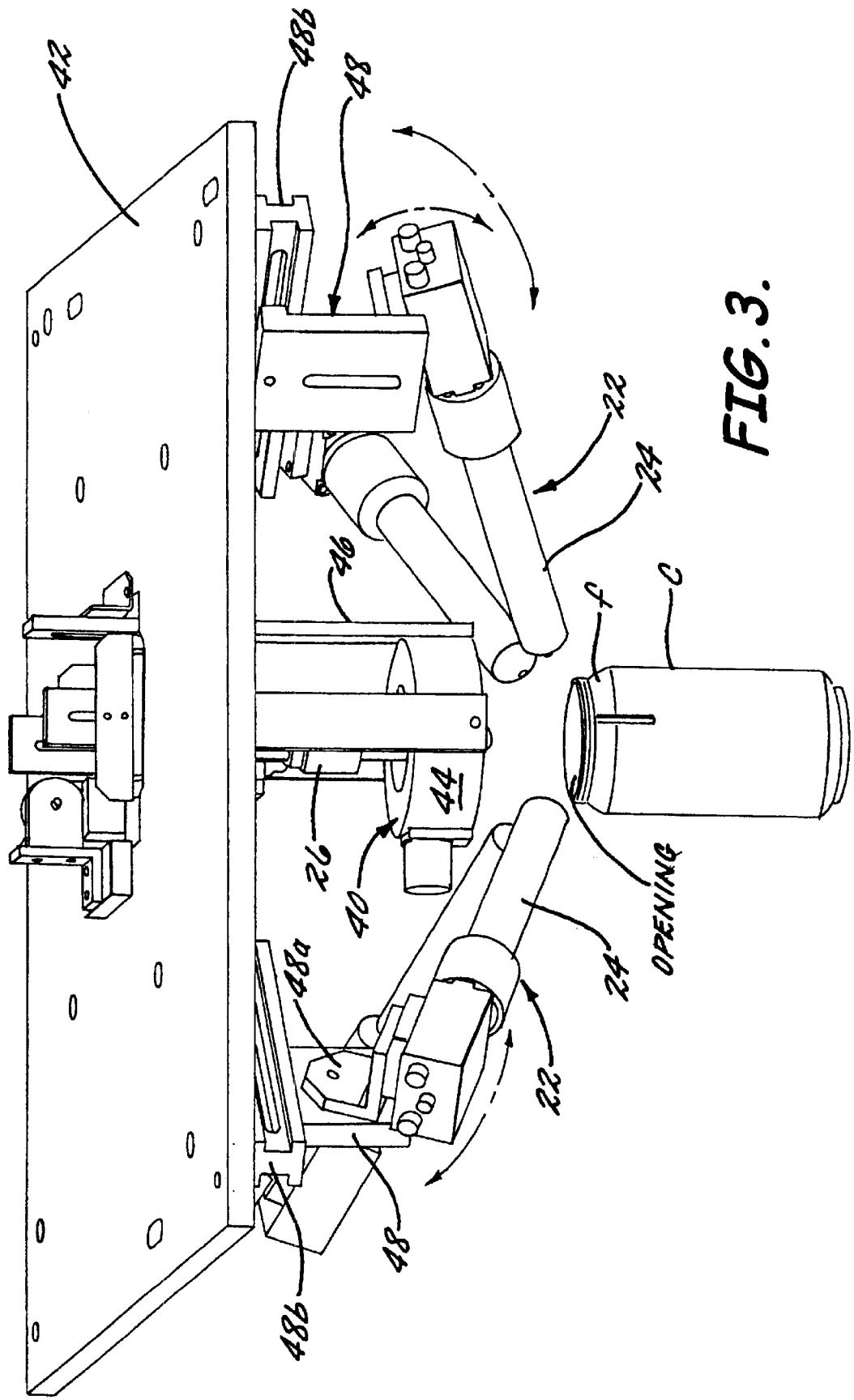
FIG. 3 is an isometric view of a portion of the inspection station showing wide angle lenses and cameras that acquire images from the side and top.
Figure 4:
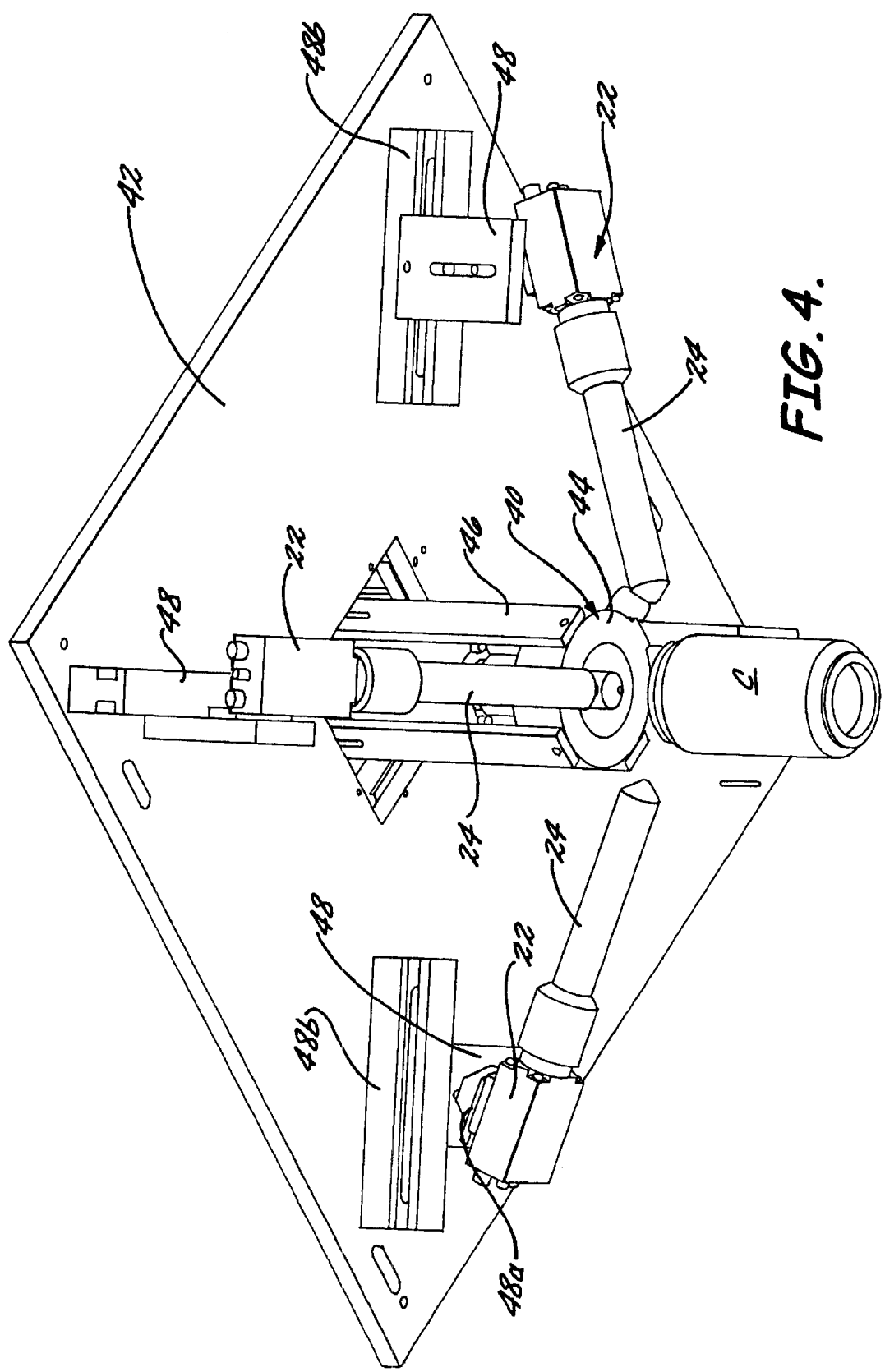
FIG. 4 is another isometric view similar to FIG. 3 and taken from a view looking toward the bottom of the can.

At the inspection station, at least one light source 40 illuminates the interior of the can, and in one example, the source is a xenon strobe instead of a more conventional prior art LED strobe. As shown in FIG. 3, a mounting plate 42 is positioned at the inspection station and the xenon strobe is mounted in the center portion of the mounting plate 42. The xenon strobe is mounted on a ring support member 44 and the top camera 26 and its wide angle lens extend downward through the ring support member, as shown in FIG. 4. The ring support member 44 is mounted by a support bracket 46 to the mounting plate.

Each of the side and top cameras are charge coupled device (CCD) cameras and work with pinhole lenses. These cameras operate in NTSC standards and typically have two frames that are interlaced at 1/60 second per frame, and having two frames per image. However, it is possible to operate the CCD cameras in the present invention in frame mode and acquire one of the frames such that the images are in half resolution down to 1/60 second, thus acquiring an image every 16 milliseconds. Naturally, other cameras could be used and the acquisition time can vary by standards known to those skilled in the art. Line scan cameras, frame cameras and other cameras can also be used. With a vertical sync pulse of 1/60 second and 256 lines, the present invention could allow up to 3,000 cans per minute. It is possible, for example, to move down to 64 lines and obtain 360 images a second, but there may be data problems in a regular type of processor that could be used in the present invention with a normal personal computer operating at a 133 megahertz bus. Although any number of processors could be used in the present invention, as known to those skilled in the art, a regular personal computer that is mounted for aesthetic and functional reasons within the base of the inspection station frame (FIG. 1) is acceptable as long as it has adequate processing power and data transfer capability as described above.

As shown in FIGS. 3–6, the side cameras 22 are mounted on side mounting brackets 48 and include the wide angle lens that points at an acute angle into the interior of the can at the top flange area (f) defined by the can. The cameras are connected to the processor 23.

The side mounting brackets 48 also include a swivel mounting bracket 48a to allow the cameras to be oriented at different angles, and also swivelled at different angles, as shown by the arrows in FIG. 3. Side mounting brackets 48 are slidable upon lateral supports 48b mounted on the underside of the mounting plate.

FIG. 7 illustrates the type of computer images that can be displayed on a computer screen using the four side cameras and top camera. Naturally the images can be displayed as part of a graphical user interface of a computer screen, and can include other information and data entry boxes (not shown) to allow further data processing on the captured images. It is also possible to display other image data as known by one skilled in the art on the graphical user interface.

Figure 14A:
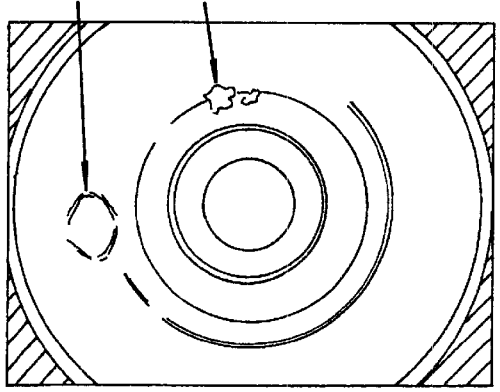
Figure 14B:
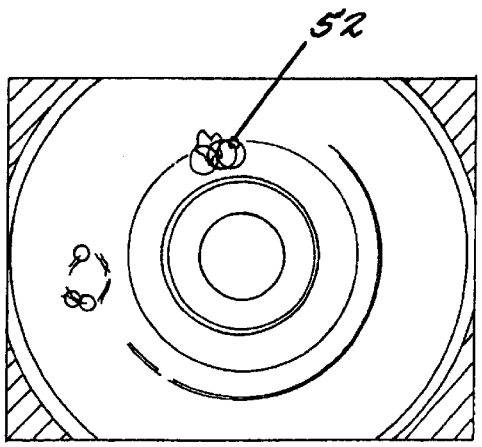

FIGS. 8A–14B show dual side-by-side images where visual images are shown on the left side, and the processed images, as seen by the computer, are shown on the right side. FIGS. 8A and 8B show neck pucker. FIGS. 9A and 9B show a hole-in-sidewall. FIGS. 10A and 10B show a sidewall crease. FIGS. 11A and 11B show a neck dent and ink stain. FIGS. 12A and 12B show an ink stain. FIGS. 13A and 13B show a thumb dent and ink stain. FIGS. 14A and 14B show a missing coating/partial spray, such as when an enamel spray has been missed.

The circles indicated at 50 are considered hits, but not considered defects, until they are processed in groups of contrast pairs, shown by the circles indicated at 52, as explained below. The sensitivity could be set very low and many false hits could be registered. The sensitivity is set with the contrast of the grayscale images. For a hit to be considered a defect, it must meet the criteria and have neighbors, a certain contrast and contrast-pairs.

Referring now to FIGS. 15–20, there are illustrated flow charts for the software algorithm that is used in the system of the present invention for inspecting containers, such as a can. Although the description of the software algorithm for the system proceeds with reference to the inspection of containers and cans, such as the common 12 ounce aluminum formed cans, the software algorithm can be used in the inspection of different articles and containers of different configurations and different types, as known to those skilled in the art.

Figure 15:
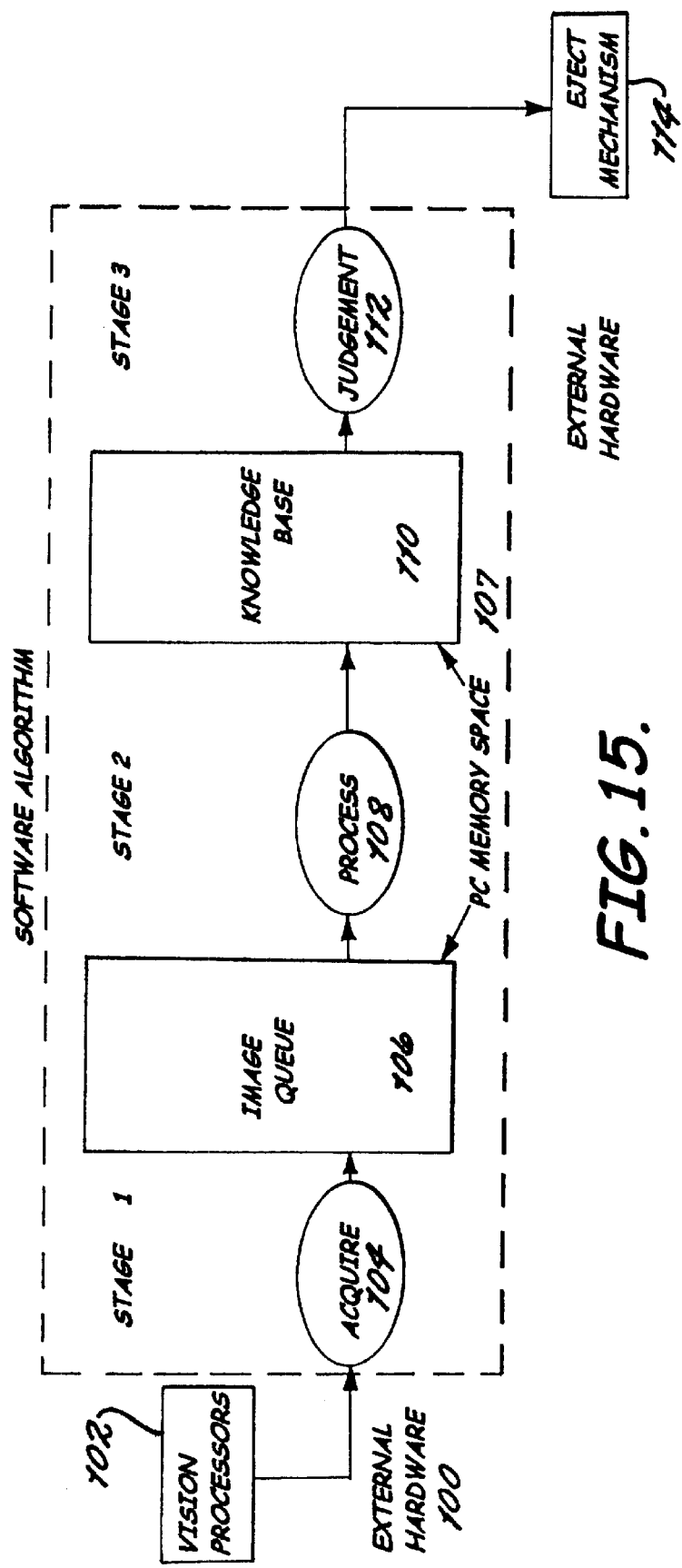
FIG. 15 is an overall block diagram showing the software algorithm as it works in a "pipeline" and parallel processing format.

The software algorithm can be written in different software languages, as known to those skilled in the art. In the present example, however, the program C++ has been found to be an advantageous language for the software. The software algorithm establishes a "pipeline" process of three processing stages as shown in FIG. 15, and uses a two pass filter as explained below. Each of the three stages function independently, but simultaneously. While the first stage is working on a first group of images, the second stage is working on a second group of images and the third stage is working on a third group of images. A single group of images must be processed literally through the pipeline.

In the illustrated figures, each of the three stages process the five images per stage, i.e., the four side images and the one top image, as shown in FIG. 7. It should be understood that the software algorithm operates in a pipeline process with the acquired groups of images. The number of images per group depends on the type of hardware used for acquiring the images, such as what type of CCD cameras or line scan cameras are used. As long as the processor and bus connections have the appropriate processing power and data capability, then a larger number of images can be acquired, if necessary.

For purposes of clarity, reference numerals used in describing the system software begin in the one hundred (100) series.

As shown in FIG. 15, and as noted before, the external hardware 100 includes the CCD cameras having associated vision processors 102 that process each acquired image. Each time there is a hardware trigger, the five cameras "grab" or acquire a respective image, totaling five images, which are passed into the software processing pipeline and processed in parallel.

In the first acquire stage 104, the image queue 106 is a memory buffer as part of a PC memory space 107. Enough memory space has been allocated to hold a set number of images, and in one example, 30 sets of images. The number of images that can be held in the image queue 106 can vary, depending on the processing speed and type of images, as known to those skilled in the art. In the second processing stage 108, the knowledge base 110 contains the rules for determining a flawed can.

The third judgment stage 112 interacts with the PC memory space 107, the knowledge base 110 and the eject mechanism hardware 114 to eject a can if the system has determined that a can or other container is flawed. Throughout these three stages, the first acquire stage 104 interacts with the vision processors 102 and PC memory space 107 containing the image queue 106. The process stage 108 interacts only with the PC memory spaces of the image queue and the knowledge base. The judgment stage 112 interacts with the PC memory space 107, the knowledge base 110, and the eject mechanism hardware 114.

Figure 16:
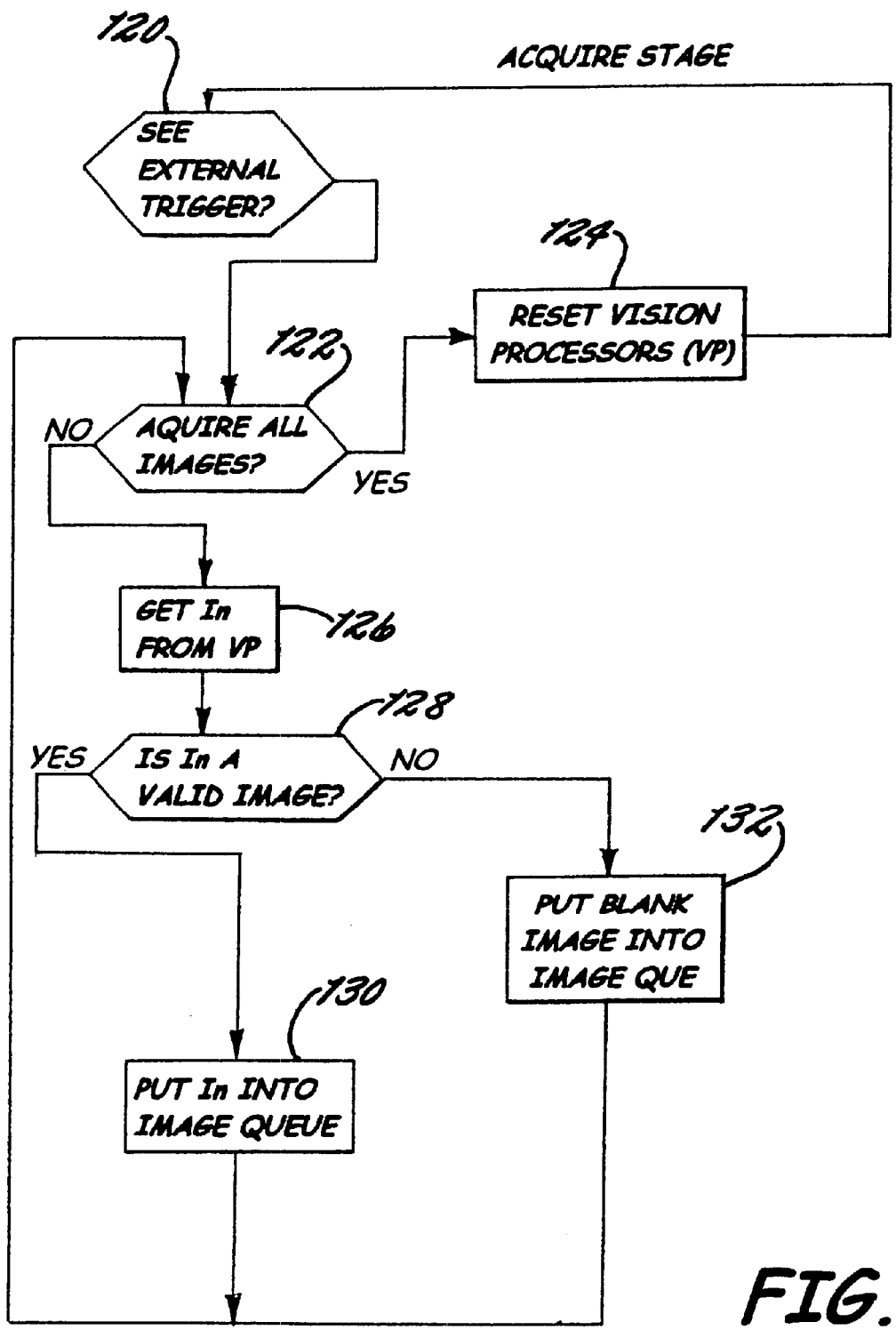
FIG. 16 is a flow chart illustrating the acquisition stage of the software that acquires an image.

The algorithm steps that are operative for the first acquire stage 104 are shown at FIG. 16. The system determines if a hardware trigger has been received (block 120) corresponding to a decision that a can is available for image acquisition. If there is no external trigger corresponding to a decision that a can is available, this step repeats until there is a trigger. If there is a trigger, the five cameras acquire all images (block 122), and if all images are acquired, the vision processors are reset (block 124). The software again waits for the external trigger.

If all images are not obtained, then any single images that have been obtained are acquired from the vision processors (block 126). This could be any number ($I_n$) of images, $I_1$, $I_2$, $I_3$ ... $I_n$. In the present hardware configuration illustrated in FIGS. 1–4, there are five cameras, and thus, $1 \leq n \leq 5$. The software determines if $I_n$ is a valid image (block 128). If $I_n$ is a valid image, then those images $I_n$ are placed into the image queue (block 130). If the images $I_n$ are not valid images, then a blank image is placed into the image queue (block 132). A blank image is used if a number $I_n$ of cameras capture good images and they are analyzed and processed, but one or more other images are a blank image, for example, such as when camera no. 5 (for example) is inoperable. A fifth image is retained as a blank image and the processor and software will not concern itself with processing that blank image at a later stage.

Figure 17:
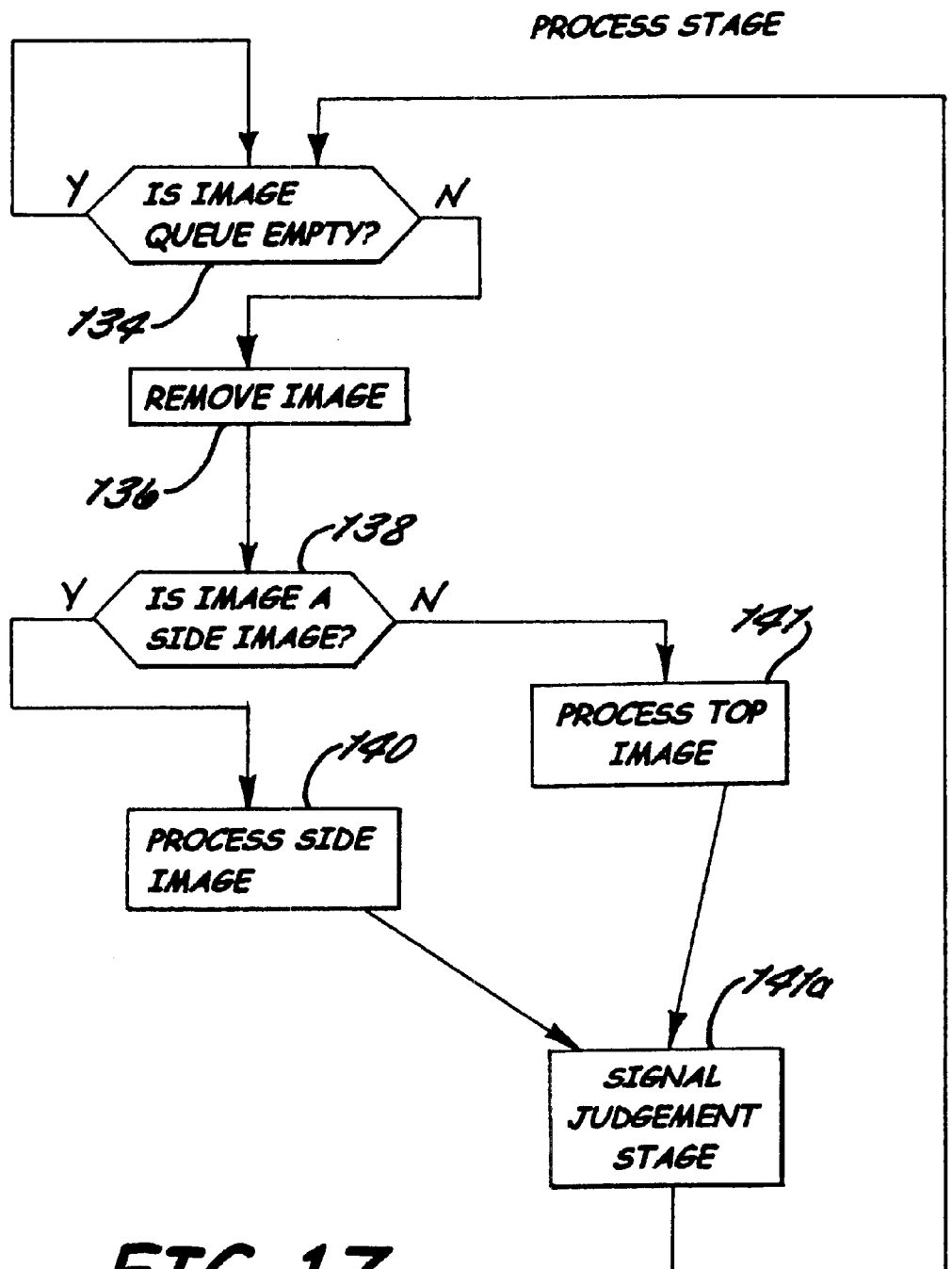
FIG. 17 is a flow chart illustrating the processing stage.
Figure 18:
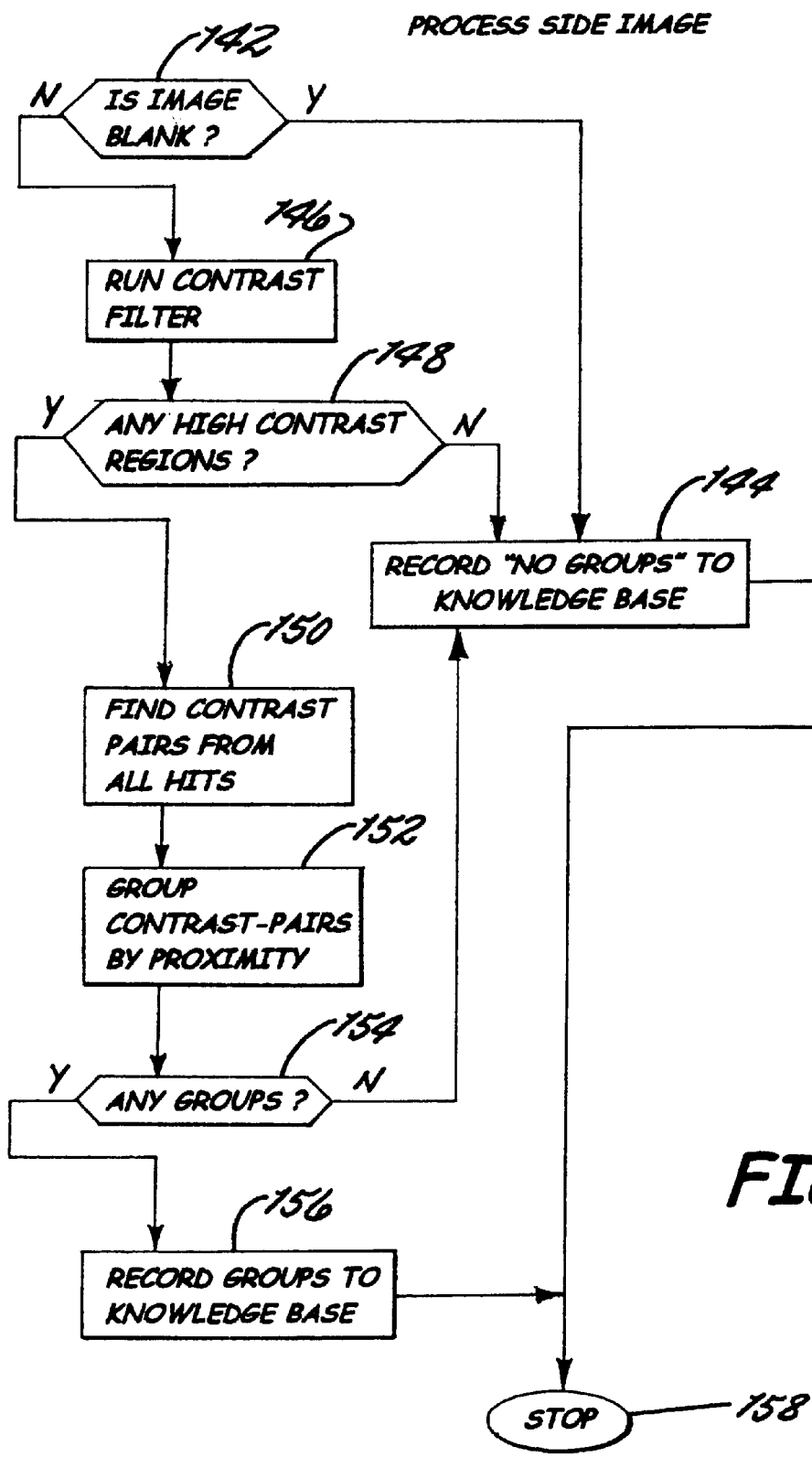
FIG. 18 is a flow chart illustrating the processing of the side image.

FIG. 17 illustrates the second process stage 108 and in the first step, a determination is made if the image queue 106 is empty. If the image queue is empty (block 134), then the software loops back and continues to look at the image queue to determine if it is empty. If the image queue is not empty, then the image is removed from the image queue (block 136) and a determination is made whether the processor is a side image 138 based upon information stored in the knowledge base concerning the side image processing. If the image is a side image, then the image is processed as a side image (block 140), as shown in the algorithm.

The side image processing first determines if the image is blank (block 142). If it is a blank image, then the software records "no groups" to the knowledge base (block 144). For example, for every can entering into the system for inspection, there is a set of information such that the judgment thread in the software determines whether to keep the can or reject the can. This is done to determine if there is can data to record in the knowledge base.

If there is no blank image, then the contrast filter is run (block 146) checking contrast based on gray scale. This is a software tool used to analyze the image space-by-space in segments, i.e., blocks of image data. Thus, the software analyzes blocks of the image data, and one at a time, determines first whether there are high contrast regions (block 148). If there are high contrast regions in the gray scale analysis, the software counts that region as a hit. Thus, the software algorithm determines if there are any high contrast regions, and if yes, it determines the contrast pairs from the different hits (block 150).

After the filter is run and the system marks the high contrast regions in the memory space of the memory array, the system determines whether there are any high contrast regions. The system software groups the contrast pairs by proximity (block 152). These high contrast regions are analyzed using gray scale imaging. For example, if the image intensity of the gray scale of blocks of image data go from white to black, that is a positive contrast difference. If the gray scale image goes from black to white, there is a negative contrast difference.

The system analyzes group pairs of approximately equal contrast that are close to each other, and if there is a defect, for example, in the neck of the can, the contrast will change from a regular dark contrast to light wherever the defect is, and then be dark again at the regular or normal can surface. Thus, the algorithm determines the changes in contrast intensity. If there are groups of contrast changes (block 154), then the groups are recorded in the knowledge base (block 156). In the previous steps, if there have been no high contrast regions, then the processor records "no groups" to the knowledge base. If after grouping the contrast pairs by proximity and there are no groups, then the processor records "no groups" to the knowledge base. In any event, at this stage, side image processing stops (block 158).

Figure 19:
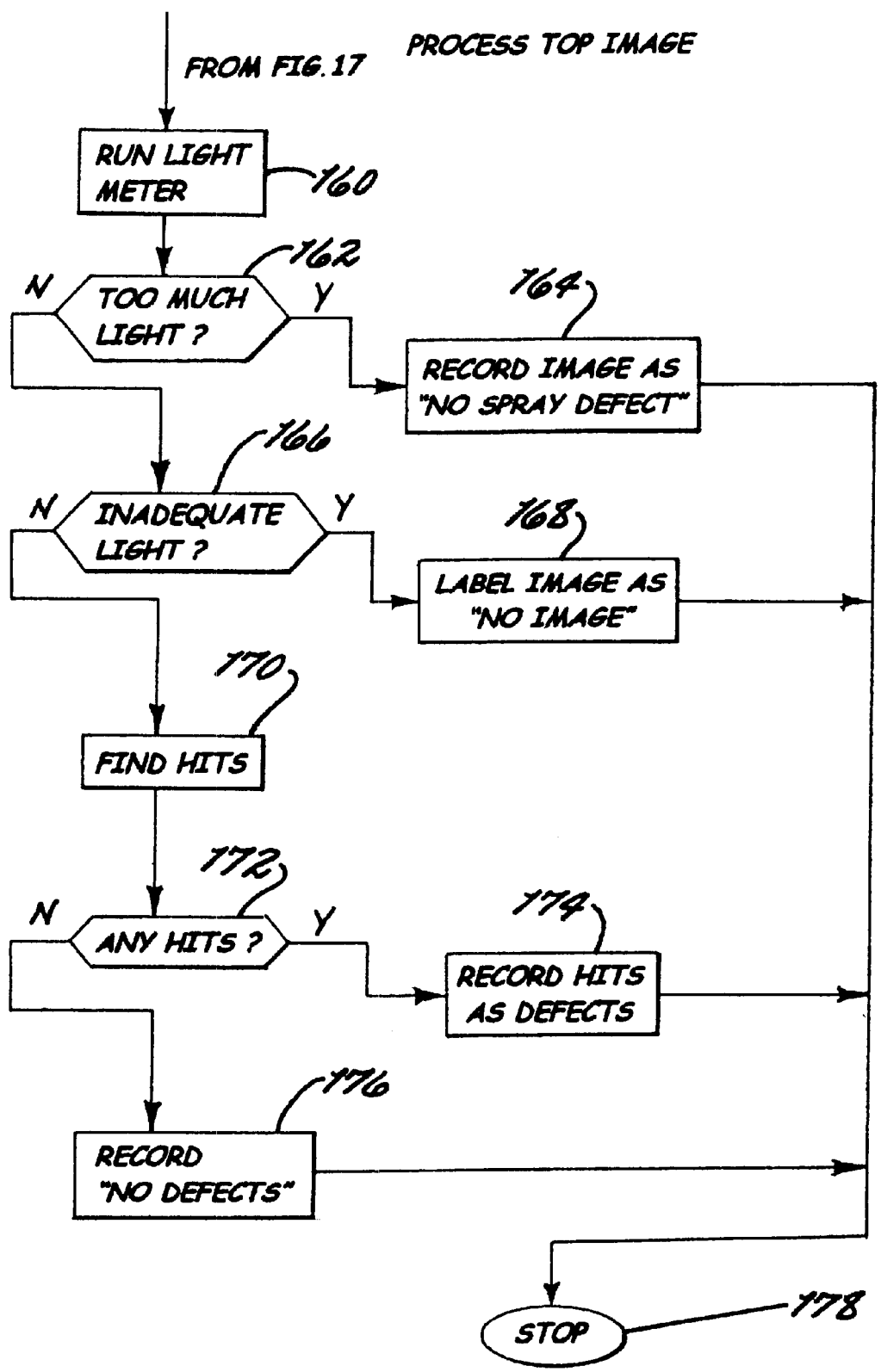
FIG. 19 is a flow chart illustrating the processing of a top image.

If the software determines that there are no side images (block 138, FIG. 17), then the image is processed as a top image (block 141), as shown in the top image processing algorithm flow chart of FIG. 19. After processing the side image and/or top image, the judgment stage is signaled (block 141A).

A light meter is run (block 160), which is a software application to determine how much light is in a specific region. The light meter is operated on the image data itself. The system software can incorporate light meter software as known to those skilled in the art. If there is too much light (block 162), then the image is recorded to reflect the container or can as a "no spray" defect (block 164). In this instance, a portion or all of the inside of the can has no enamel or other protective coating, and at least one camera has been receiving an image of raw aluminum, which floods the image intensity out through massive reflection. It is termed a "no spray" defect corresponding to the lack of enamel spraying.

Figure 20:
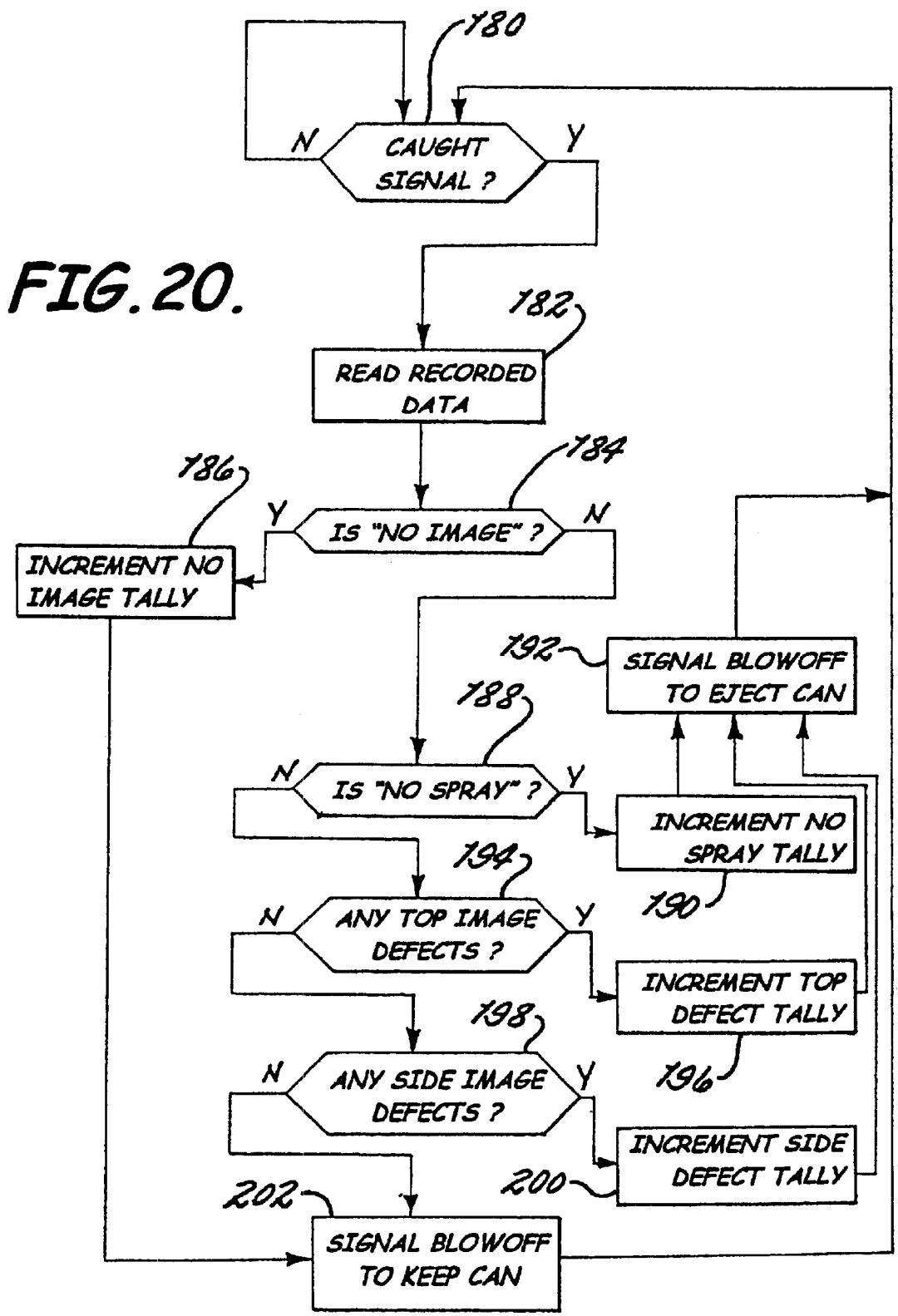
FIG. 20 is a flow chart illustrating the decision making process for accepting or rejecting the container after the previous acquisition and processing stages.

If there is not excessive light, then the system determines if there is inadequate light (block 166). If there is inadequate light, then the label image is tagged a "no image" (block 168). "No image" can occur, for example, when a strobe light has failed. The third judgment stage 112 analyzes this information and raises a flag indicating that there is a problem, especially if subsequent images are processed linearly, each having too little light. The same could occur if too much light, and the images are referenced as corresponding to surfaces that are "no spray" defect. The system determines the hits (block 170), and if there are any hits (block 172), these hits are recorded as defects (block 174). If not, then the processor records "no defects" (block 176). At this point, the processing stage stops (block 178) and the judgment stage is then signaled and processing begins in the third judgment stage as shown in FIG. 20.

The system software determines if a judgment stage signal is caught (block 180). If no signal is caught, then the system software continues in a loop to determine when a judgment stage signal is received. If the signal is received and caught, the recorded data is read from the knowledge base (block 182). If there is a "no image" reference (block 184), then the tally for "no images" are incremented (block 186), in order to keep track of the cans. If not, then the system software determines if there is a "no spray" data reference (block 188), and if there is, then the "no spray" tally is incremented (block 190). A signal blow off occurs (block 192) to eject the can at this point. If the "no spray" determination (block 188) is negative, then the system determines if there are any top image defects (block 194), and if there are, the top defect tally is incremented (block 196) and the signal generated to blow off and eject the can (block 192). If there are no top image defects, then the system determines if there have been any side image defects (block 198), and if there have been, then the side defect tally is incremented (block 200) and the signal generated to blow off and eject the can (block 192). If there are no side image defects, then the signal blow off is not signaled and the can remains on line for further processing (block 202).

It is evident that the algorithm is advantageous with its use of filters and decision processes to determine the positive and negative contrasts, and is more advantageous than prior art units.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A system for inspecting an object having an annular opening comprising:

a plurality of cameras that acquire grayscale image data of arcuate sectors that together comprise a circumferential area within the opening; and a processor connected to the plurality of cameras for receiving the grayscale image data and determining defects within the object using a pipeline process of independent processing stages on image data with a rules based knowledge base by acquiring true and false hits in a first processing stage based on a low sensitivity that is set with contrast of grayscale images, and in a subsequent processing stage, determining contrast regions in a computer memory space from the true and false hits and grouping contrast pairs by proximity, analyzing contrast pairs of about equal contrast that are close to each other to determine changes in contrast intensity, recording groups of contrast changes in a knowledge base while also processing image data to determine how much light is in a specific region to determine if adequate light was present, and in a judgment stage, processing the contrast changes in a rules based knowledge base to determine defects as coherent structural defects.

2. A system according to claim 1, and further comprising a camera positioned substantially above the opening for acquiring a top grayscale image of the opening.

3. A system according to claim 2, in the object, wherein said processor determines defects from the top grayscale image and the grayscale images of arcuate sectors simultaneously.

4. A system according to claim 1, and further comprising a memory associated with said processor for storing within a knowledge base rules for determining when a defect exists based on contrast differences in grayscale intensity.

5. A system according to claim 1, wherein said cameras comprises charge coupled device cameras.

6. A system for inspecting cylindrical containers having top container openings comprising:
- a conveyor for advancing a plurality of cylindrical containers along a predetermined path of travel into an inspection station;
- a strobe light positioned at the inspection station for illuminating the container opening;
- a plurality of cameras positioned at the inspection station for simultaneously acquiring grayscale image data of arcuate sectors that together comprise a circumferential area within the opening; and
- a processor connected to the plurality of cameras for receiving the grayscale image data and determining defects within the container using a pipeline process of independent processing stages on image data with a rules based knowledge base by acquiring true and false hits in a first processing stage based on a low sensitivity that is set with contrast of grayscale images, and in a subsequent processing stage, determining contrast regions in a computer memory space from the true and false hits and grouping contrast pairs by proximity, analyzing contrast pairs of about equal contrast that are close to each other to determine changes in contrast intensity, recording groups of contrast changes in a knowledge base while also processing image data to determine how much light is in a specific region to determine if adequate light was present, and in a judgment stage, processing the contrast changes in a rules based knowledge base to determine defects as coherent structural defects.

7. A system according to claim 6, and further comprising an eject mechanism for ejecting a container from the conveyor after determining that any defects are serious enough to make the container defective.

8. A system according to claim 7, wherein said eject mechanism comprises an air blow off mechanism.

9. A system according to claim 6, wherein said conveyor includes a vacuum assist mechanism to aid in retaining containers onto the conveyor by vacuum.

10. A system according to claim 6, and further comprising a camera positioned at the inspection station having a field of view into the container opening for acquiring a top grayscale image of the surface interior through the container opening.

11. A system according to claim 10, wherein said processor determines defects from grayscale images of arcuate sectors and the top grayscale image simultaneously.

12. A system according to claim 6, wherein said cameras comprise charge coupled device cameras.

13. A system according to claim 6, and further comprising a memory associated with said processor for determining when a defect exists based on contrast differences in grayscale intensity.

14. A method of inspecting an object having an opening comprising the steps of:
- acquiring grayscale image data of arcuate surface sectors that together comprise a circumferential area inside the opening of the object; and
- processing the grayscale image data to determine defects of the object using a pipeline process of independent processing stages on image data with a rules based knowledge base by acquiring true and false hits in a first processing stage based on a low sensitivity that is set with contrast of grayscale images, and in a subsequent processing stage, determining contrast regions in a computer memory space from the true and false hits and grouping contrast pairs by proximity, analyzing contrast pairs of about equal contrast that are close to each other to determine changes in contrast intensity, recording groups of contrast changes in a knowledge base while also processing image data to determine how much light is in a specific region to determine if adequate light was present, and in a judgment stage, processing the contrast changes in a rules based knowledge base to determine defects as coherent structural defects.

15. A method according to claim 14, and further comprising the step of acquiring the grayscale images simultaneously.

16. A method according to claim 15, and further comprising the step of processing the grayscale images simultaneously in parallel.

17. A method according to claim 14, and further comprising the step of determining contrast differences in the grayscale intensity of each grayscale image for determining defects.

18. A method according to claim 14, and further comprising the step of acquiring each grayscale image with a camera.

19. A method according to claim 14, and further comprising the step of acquiring a top grayscale image of the opening.

20. A method of inspecting a cylindrical container having an annular opening comprising the steps of:
- simultaneously acquiring grayscale image data of arcuate surface sectors inside the container opening that together comprise a circumferential surface area of the container opening;
- processing the grayscale image data to determine defects of the container by using a pipeline process of independent processing stages on image data with a rules based knowledge base by acquiring true and false hits in a first processing stage based on a low sensitivity that is set with contrast of grayscale images, and in a subsequent processing stage, determine contrast regions in a computer memory space from the true and false hits and grouping contrast pairs by proximity, analyzing contrast pairs of about equal contrast that are close to each other to determine changes in contrast intensity, recording groups of contrast changes in a knowledge base while also processing image data to determine how much light is in a specific region to determine if adequate light was present, and in a judgment stage, processing the contrast changes in a rules based knowledge base to determine defects as coherent structural defects.

21. A method according to claim 20, and further comprising the step of recording the changes in contrast intensity within a knowledge base of a computer memory.

22. A method according to claim 20, and further comprising the step of acquiring each grayscale image by capturing the image with a camera.

23. A method according to claim 22, wherein said camera comprises a charge coupled device camera.

24. A method according to claim 22, and further comprising the step of directing the camera a side angle relative to the container opening.

25. A method according to claim 22, wherein each arcuate sector comprises a quadrant of the container opening.

26. A method according to claim 20, and further comprising the step of acquiring a top image of the container opening.

27. A method according to claim 20, and further comprising the step of illuminating the interior of the container opening with strobe light.

28. A method according to claim 27, wherein the strobe light comprises a Xenon strobe light.

29. A method of inspecting cylindrical containers having annular container openings comprising the steps of:

advancing a plurality of cylindrical containers along a predetermined path of travel into an inspection station;

illuminating the interior of the container opening;

simultaneously acquiring grayscale image data of arcuate surface sectors inside the container opening that together comprise a circumferential surface area of the container opening;

processing the grayscale image data to determine defects of the container by using a pipeline process of independent processing stages on image data with a rules based knowledge base by acquiring true and false hits in a first processing stage based on a low sensitivity that is set with contrast of grayscale images, and in a subsequent processing stage, determining contrast regions in a computer memory space from the true and false hits and grouping contrast pairs by proximity, analyzing contrast pairs of about equal contrast that are close to each other to determine changes in contrast intensity, recording groups of contrast changes in a knowledge base while also processing image data to determine how much light is in a specific region to determine if adequate light was present, and in a judgment stage, processing the contrast changes in a rules based knowledge base to determine defects as coherent structural defects.

30. A method according to claim 29, and further comprising the step of rejecting a container by ejecting the container from the predetermined path of travel with air.

31. A method according to claim 29, and further comprising the step of advancing the plurality of cylindrical containers by a conveyor.

32. A method according to claim 29, and further comprising the step of recording the changes in contrast intensity within a knowledge base as part of a computer memory.

33. A method according to claim 29, and further comprising the step of acquiring each grayscale image by capturing the image with a camera.

34. A method according to claim 33, wherein said camera comprises a charge coupled device camera.

35. A method according to claim 33, and further comprising the step of directing said camera at side angle relative to the container opening.

36. A method according to claim 29, wherein each arcuate sector comprises a quadrant of the container opening.

37. A method according to claim 29, and further comprising the step of acquiring a top grayscale image of the container opening.

38. A method according to claim 29, and further comprising the step of illuminating the interior of the container opening with strobe light.

39. A method according to claim 38, and further comprising the step of energizing the strobe to illuminate when an image is acquired.

* * * * *

UNITED STATES PATENT AND TRADEMARK OFFICE
CERTIFICATE OF CORRECTION

PATENT NO.    : 6,525,333 B1
DATED         : February 25, 2003
INVENTOR(S)   : Hooker et al.

It is certified that error appears in the above-identified patent and that said Letters Patent is hereby corrected as shown below:

Column 1,
Line 64, delete "he" substitute -- the --

Column 3,
Line 50, delete "hen" substitute -- when --

Signed and Sealed this

Fifteenth Day of April, 2003

JAMES E. ROGAN
*Director of the United States Patent and Trademark Office*